United States Patent [19]

Sheffield et al.

[11] Patent Number: 4,889,722

[45] Date of Patent: Dec. 26, 1989

[54] METHOD FOR INHIBITING POST-SURGICAL ADHESION FORMATION BY THE TOPICAL ADMINISTRATION OF TISSUE PLASMINOGEN ACTIVATOR

[75] Inventors: Warren D. Sheffield, Levanon, N.J.; Gere S. diZerega, Pasadena, Calif.

[73] Assignee: Ethicon, Inc., Somerville, N.J.

[21] Appl. No.: 157,818

[22] Filed: Feb. 19, 1988

Related U.S. Application Data

[63] Continuation-in-part of Ser. No. 924,723, Oct. 29, 1986, abandoned, which is a continuation-in-part of Ser. No. 809,536, Dec. 16, 1985, abandoned.

[51] Int. Cl.⁴ ............... A61K 9/06; A61K 37/54; A61L 2/00
[52] U.S. Cl. ............... 424/450; 424/78; 514/8; 514/21
[58] Field of Search ............... 530/350, 380, 395, 827; 435/70, 172.3, 240.1; 514/2, 8, 21; 424/450, 78

[56] References Cited

U.S. PATENT DOCUMENTS 3,755,558  9/1973  Scriliner ............... 424/47
4,615,885  10/1986  Nakagame ............... 424/94

FOREIGN PATENT DOCUMENTS 0041449  5/1981  European Pat. Off. .
219076  10/1986  European Pat. Off. .
2042556  2/1980  United Kingdom .

OTHER PUBLICATIONS

Gazzaniga, et al. "Prevention of Peritoneal Adhesions in the rat," Arch. Surg. 1975 110(4) 429–32.
Mezei et al. "Liposomes, a selective drug delivery system for the topical route of administration: gel dosage form," J. Pharm. Pharmacol, 1982 34(7) 473–4.

*Primary Examiner*—John Kight
*Assistant Examiner*—Nathan M. Nutter

[57] ABSTRACT

Postsurgical adhesion formation is inhibited by the topical administration to the site of surgical trauma of a composition comprising tissue plasminogen activator.

15 Claims, No Drawings

METHOD FOR INHIBITING POST-SURGICAL ADHESION FORMATION BY THE TOPICAL ADMINISTRATION OF TISSUE PLASMINOGEN ACTIVATOR

This application is a continuation-in-part of our co-pending application Ser. No. 924,723, filed on Oct. 29, 1986 and now abandoned, which was a continuation-in-part of our application Ser. No. 809,536, filed Dec. 16, 1985 now abandoned.

The invention relates to a method for inhibiting post-surgical adhesion formation.

BACKGROUND OF THE INVENTION

Adhesion formation is a major post-surgical complication with no practical solution. The incidence of adhesion formation following surgery approaches 100 percent, according to some sources, with a clinically significant complication rate of about 5 to 10 percent, depending on the type of surgery. Among such complications are bowel obstruction, infertility, and pain. Occasionally, adhesions necessitate a second operative procedure to remove the adhesion, which may in turn further aggravate the problem.

Because of the seriousness of the problem, much medical research has been performed in efforts to find ways to combat adhesions. See, for instance, Stangel et al., "Formation and Prevention of Postoperative Abdominal Adhesions", the Journal of Reproductive Medicine, Vol. 29, No. 3, March 1984 (pp. 143–156), and diZerega, "The Cause and Prevention of Postsurgical Adhesions", published by Pregnancy Research Branch, National Institute of Child Health and Human Development, National Institutes of Health, Building 18, Room 101, Bethesda, Md. 20205. Among the approaches that have been tried for preventing post-surgical adhesion are the following:

Systemic administration of ibuprofen (e.g., see Singer, U.S. Pat. No. 4,346,108);
Parenteral administration of antihistamines, corticosteroids, and antibiotics;
Intraperitoneal administration of dextran solution and of polyvinylpyrrolidone solution; and
Systemic administration of oxyphenbutazone, a non-steroidal anti-inflammatory drug that acts by inhibiting prostaglandin production.

Corticosteroids have been administered intraperitoneally as well as systemically in efforts to prevent adhesions. (See the Stangel et al. article, cited above, on p. 147, as well as the articles cited therein.) Some studies have questioned the efficacy of corticosteroids in adhesion prevention. In high doses, these materials may suppress the immune system and interfere with wound healing. Therefore, the use of corticosteroids does not seem to be an acceptable solution to the post-operative adhesion problem.

BRIEF SUMMARY OF THE INVENTION

The invention comprises a method for inhibiting the formation of post-surgical adhesions in mammals (including humans) which method comprises the topical locally effective administration of an effective amount of a composition including as an active ingredient tissue plasminogen activator ("t-PA") to the injured tissue surface site of surgical trauma, for a period of time sufficient to inhibit the formation of post-surgical adhesions.

PRIOR ART

Kapur et al., in "Prevention of Reformation of Peritoneal Adhesions", Arch. Surg., Vol. 105, Nov. 1972 (pp. 761–764), disclose the systemic administration of proteolytic enzymes from carica papaya to combat adhesions.

Singh, in U.S. Pat. No. 3,912,704, suggests that a protease inhibitor isolated from horse urine may be useful in preventing the formation of post surgical adhesions.

The use of streptokinase, streptodornase, and urokinase in preventing adhesions has been reported. Administration was by a single intraperitoneal dose. The references are:

Ascherl et al., PREVENTION OF INTRAPERITONEAL ADHESIONS WITH A FIBRINOLYTIC, Medwelt, 34, No. 13/83, pp. 410–415;
Mund-Hoym et al., PREVENTION OF POSTOPERATIVE ADHESIONS-AN ANIMAL STUDY, Geburtsh, u. Franenheilk, 44 (1984), pp. 463–467; and
Minju et al., ANIMAL STUDIES ON THE PREVENTION OF ADHESION AND ADHESIVE INTESTINAL OBSTRUCTION AFTER ABDOMINAL OPERATIONS IN RATS, Acta Acadeniae Medicinae Wuhan, 3, (2), pp. 77–83.

(The publication dates of the Ascherl et al. and Minju et al. articles are not known. The translations have the dates "7/18/85" printed on the title pages. It is possible that these two publications are not prior art to applicants.)

Human fibrinolysin has been evaluated, either alone or combined with other medicaments, to combat post-surgical adhesions. See Gazzaniga et al., Arch. Surg. Vol. 110, pp. 429–432 (1975), and references cited therein.

Other authors have reported that fibrinolytic agents have either not been successful in preventing adhesions, or the risks associated with their use were too high. In this connection, see, for instance, the following articles:

Holtz, "Prevention of Postoperative Adhesions", The Journal of Reproductive Medicine, Vol. 24, No. 4, April 1980, pp. 141–146, esp. p. 144; and
Rivkind et al., Eur. Surg. Res. (Switzerland), 1985, Vol. 17, No. 4, pp. 254–8.

Buckman et al., in "A Unifying Pathogenetic Mechanism in the Etiology of Intraperitoneal Adhesions", Journal of Surgical Research, Vol. 20, No. 1, January 1976 (pp. 1–5), theorized that post-surgical adhesion formation in the peritoneal cavity was associated with trauma or ischemia induced reduction in plasminogen activator activity.

DETAILED DESCRIPTION OF THE INVENTION

The pharmacologically active composition employed in this invention is tissue plasminogen activator. t-PA is a product that is normally present in the body, where it plays a role in the lysis of thrombi. There is some evidence that in its "storage mode" in the body, t-PA exists in the single stranded form. t-PA can also exist in a double stranded form. Both forms have a high affinity for fibrin, a component of thrombi. Upon being bound to fibrin, the single stranded form of t-PA appears to be converted to the double stranded form. Both the single stranded and double stranded forms of t-PA can be used in this invention. Natural t-PA is glycosolated and contains associated carbohydrates or oligosaccharides at the glycosylated sites. Both the degree of glycosolation and the number of and specific nature of the associated carbohydrates or oligosaccharides are believed to vary normally, and can also vary with the t-PA employed in this invention.

t-PA can be isolated from human tissue, and more recently has been produced using recombinant DNA technology. See, for instance, Goeddel et al., UK Patent Application GB 2 119 804 A, published Nov. 23, 1983, Gill, European Patent Application No. 0 174 835, published Mar. 19, 1986, and Mori et al., European Application No. 0 100 982, published Feb. 22, 1984, for various methods of isolating t-PA from tissue or producing it by r-DNA techniques.

In accordance with the process of the invention, the active agent is applied topically to the site of surgical trauma in effective amounts for a period of time sufficient to inhibit the formation of post-surgical adhesions. It is preferably administered before significant wound healing has begun. It is preferred and most convenient to administer the active agent in a single dose application during the surgery prior to closing the surgical field. In most cases, the time of administration of a single dose would be just prior to closing; however, in some cases it may be desired to administer the composition earlier during the surgical procedure. In some situations it may be desired to administer the active agent continually over a period of time, as would be the case if the active agent were administered by a catheter or in a sustained release formulation. The specification, below, describes some methods that can be used to determine the optimum periods of administration when the mode of application is continual, as by catheterization (in the animal models used, an implanted osmotic mini-pump was used—this procedure is analogous to catheterization in a human). However, the most convenient mode of administration is via a single dose application of the active agent prior to closing the surgical field (as indicated above, in most cases this time of administration would be just prior to closing).

By the term "topically", is meant that the t-PA is administered non-systemically to the surface of the tissue (internal or, in some cases, external) to be treated. The treatment is intended to be "locally effective", that is, the treatment is intended to affect the tissue treated or adjacent or neighboring tissue. The term "site of surgical trauma" is meant to include the site of tissue that has been injured in any way, and includes, for example, tissue sites that have undergone incision, excision, drying, suturing, fulgeration, cauterization, abrasion, contusion, manipulation, laceration, anastomosis, prosthetic surgery, curettage, orthopedic surgery, neurosurgery, cardiovascular surgery, or plastic or reconstructive surgery. "Site of surgical trauma" also includes tissue that is adjacent to the injured tissue. In some cases, effective treatment may be obtained simply by the topical application of t-PA to tissue near that which has been surgically manipulated.

The method of the invention is useful in any surgical procedure in which it is desired to inhibit the formation of post-surgical adhesions. It is thus broadly useful in all types of surgery in which adhesion formation can be a complication. For instance, the invention is useful in abdominal surgery, in gynecological surgery, in thoracic surgery, in cardiovascular surgery, in orthopedic surgery affecting tendons, ligaments, etc., in neurological surgery affecting the dura mater, and the like.

The t-PA may be administered to the site of surgical trauma by any convenient mode such as, for example, by lavage, by catheter, by coating directly on the site in a salve, ointment, gel, cream, aqueous surface active composition, emulsion, suspension, film, or foam, or by any other convenient mode. The site can be contacted directly, as by applying a salve, ointment, gel, etc., or in some cases the medicament can be introduced to a site near the site of trauma and natural migration of fluids will serve to carry the medicament to the desired site. Such natural migration of fluids can occur, for instance, intraperitoneally, in response to peristaltic contraction of the intestines.

The t-PA is ordinarily administered in a sterile formulation in a pharmaceutically acceptable carrier or vehicle such as phosphate buffered saline ("PBS"), isotonic saline, purified water, an organic carrier (which may be in an aqueous solution or suspension) such as a proteoglycan, for example a glycosaminoglycan such as hyaluronic acid or a derivative thereof (such as a pharmaceutically acceptable salt or ester thereof) or a similar polysaccharide such as chitosan or a derivative thereof, a lipid, for example, a phospholipid micelle or vesicle (the lipid may simply be a mixture of a phospholipid in water), dextran, a cellulosic material, polymers such as polyacrylamide or p-dioxanone, lactide, and/or glycolide based absorbable polymers, (the polymer may be in the form of microcapsules or it may be incorporated in a salve- or ointment-like formulation or a gel or gel-like composition), or in an aqueous solution of a surface active agent such as a polyoxyethylene-polyoxypropylene block copolymer or a sorbitan fatty acid ester-polyoxyethylene ether. Sterilization of the formulation may be accomplished in the usual ways, including aseptic preparation, filtration, exposure to gamma radiation, autoclaving, and the like.

In one aspect of the invention, the t-PA is contained in a controlled or sustained release carrier that is capable of releasing the active drug for a period of at least [one] a few hours (e.g., one to three hours) and up to about seven days. However, the preferred and most convenient mode of administration is via a single dose application, which is usually made at the conclusion of the surgical procedure prior to closing. The preferred vehicle for such single dose applications is a gel-like or salve-like composition such as an aqueous solution or suspension of a material such as a phospholipid, hyaluronic acid or a derivative thereof (such as sodium hyaluronate), polyacrylamide, a cellulosic material, or the like.

Methods for incorporating drugs in phospholipid carriers are known in the art. For instance, one procedure for encapsulating a drug in a phospholipid vesicle is the following:

a lipid or mixture of lipids such as lecithin or other phospholipid, which may be mixed with cholesterol or other lipoid substance, is dissolved in a substantially water-immiscible organic solvent such as diethyl ether; and an aqueous phase containing the material to be encapsulated (in this case, t-PA) is added to the lipid solution, and the mixture is agitated as by exposing it to ultrasonic sound waves (sonicated). Preferably, the organic solvent is removed during sonication, as by use of heat or vacuum or both, although in some cases the solvent can be removed after the sonication. This procedure typically produces a unilamellar vesicle.

Another procedure for producing a phospholipid vesicle (in this case a multilamellar vesicle "MLV") containing a medicament is to form a film of dry lipid, as by evaporating the solvent from an organic solvent solution containing a lipid to form a film on the walls of the vessel containing the solution, and then stirring in the aqueous phase containing the t-PA to be encapsulated. (The evaporation can be done by spray drying or by vacuum evaporation, or by any other convenient method.) Free unencapsulated t-PA can be separated from MLV's by centrifugation at, e.g., 12,000 rpm.

The vesicle containing the t-PA may be dehydrated, as by freeze drying, after preparation, in order to enhance long term storage stability. The aqueous vesicle suspension can be reconstituted just prior to use by adding sterile phosphate buffered saline, sterile water, or the like.

The use of multilamellar vesicles of comparatively large size (e.g., from about 1 to about 10 microns) appears to be preferable in order to increase the dwell time of the vesicle containing the t-PA in the peritoneal cavity (or other body cavity). It is also preferred to use a pure or synthetic phosphatidylcholine in which the fatty acid moieties in the phosphatidylcholine are derived from a single fatty acid, in preparing the vesicle instead of natural lecithin, which is ordinarily a mixture of compounds. The fatty acid moieties in the liposomes are usually derived from $C_{12}$ to $C_{24}$ fatty acids, and preferably from $C_{14}$ to $C_{20}$ unsaturated fatty acids.

The following U.S. patents describe the preparation, by various procedures, of phospholipid vesicles containing various medicaments:

| | |
|---|---|
| Rahman | No. 3,993,754 |
| Lenk et al. | No. 4,522,803 |
| Baldeschwieler et at. | No. 4,310,505 |
| Mezei et al. | No. 4,485,054 |
| Gersonde et al. | No. 4,452,747 |
| Kelly | No. 4,356,167 |
| Papahadjopoulos et al. | No. 4,241,046 |
| Suzuki et al. | No. 4,016,100 |
| Sache et al. | No. 4,239,754 |
| MacDonald | No. 4,532,089 |

See also Callahan et al., European Patent Application No. 0126580, published Nov. 28, 1984, and Gregoriadis, "The Carrier Potential of Liposomes In Biology and Medicine", New England Journal of Medicine, Vol. 295, pp. 704–710 and pp. 765–770 (Sept. 23 and 30, 1976).

The foregoing are incorporated herein by reference as general procedures which can be utilized for the incorporation of t-PA in liposomes.

Other procedures for containing drugs in phospholipids (micelles or liposomes) are described in Sears, U.S. Pat. Nos. 4,426,330 and 4,145,410, and Sears et al., U.S. Pat. No. 4,298,594, the disclosures of which are incorporated herein by reference.

It is not essential that the t-PA active ingredient used in the invention be encapsulated in an inside compartment of the carrier as will normally be the case when the carrier is a phospholipid vesicle. In some cases it is acceptable for the t-PA to be dissolved or otherwise distributed more or less evenly throughout the carrier.

The t-PA is administered to the site of surgical trauma in effective quantities for a period of time sufficient to inhibit the formation of post-surgical adhesions, which Period varies from patient to patient and with the type of surgical trauma encountered. It has been found that in many cases the t-PA need be administered only during the initial stages of the wound healing process, and therefore the duration of the administration in such cases may be only a few hours, e.g., as short as from about one to three hours. In other cases, the duration of administration may be from about one or two and up to five days, and in some cases up to seven days or more, post-operatively. The examples below illustrate procedures for determining the order of magnitude of effective quantities of the drug and the period of time over which the drug is administered for effective results.

The following studies use rabbit models to illustrate the adhesion inhibition effectiveness of the topical administration of t-PA to the site of surgical trauma:

STANDARDIZED SURGICAL INJURY

New Zealand white female rabbits (1.8–2.0 kg) underwent midline laparotomy using acelepromazine and ketamine anaesthesia. A $3 \times 5$ cm flap of parietal peritoneum (about 1 mm thick) was sharply dissected from the right lateral peritoneal side-wall. The serosal surface of the adjacent large bowel was abraded with a scalpel until punctate bleeding developed. This area between the excised parietal peritoneum and adjacent large bowel serosa was then used for evaluating the efficacy of t-PA for adhesion prevention. A second incision of parietal peritoneum covering the same total area (about 15 $cm^2$) was performed in some of the rabbits 1.5–2.0 cm inferior to the initial test site along the right lateral peritoneal side-wall. Abrasion of the adjacent large bowel serosa was performed as described above for the treatment site. This second area was used as a non-treated control site to determine the effectiveness of the surgical procedure in producing adhesions, and the response to vehicle controls.

Alzet mini pumps (model 2ML1, 2 ml volume, pumping rate 10 microliters per hour, Alza, Palo Alto see U.S. Pat. No. 3,995,631) containing phosphate buffered saline with varying doses of tissue plasminogen activator (Genentech, South San Francisco, Calif.—the Genentech t-PA employed was predominantly double stranded t-PA) were sewn into the right dorsal subcutaneous space with Vicryl sutures placed 3–5 mm from each end of the pump. The polyethylene catheter tip leading from the pump into the peritoneal cavity was placed 2–3 mm over the injury test site. The catheter was secured by two 300 Vicryl sutures placed outside the site of injury. A similar pump and catheter system containing only Ringer's lactate was implanted in the middle portion of the inferior (control) test site.

Seven days after the day of abrasion, the rabbits were sacrificed by pentobarbital overdose. The extent of adhesions was evaluated as follows:
1. No adhesions
2. Filmy adhesions (separable)
3. Mild adhesions (not separable—covering up to about 35% of the test area)
4. Moderate adhesions (not separable—covering about 35 to 60% of the test area)
5. Severe adhesions (not separable—covering greater than about 60% of the test area)

The evaluation ratings set forth above are useful in the context of comparing the efficacy of various means for inhibiting the formation of adhesions. A rating of "1" is the objective, since clinical complications can result from even mild adhesions, although such complications are considered to be more likely to occur with severe adhesions than with mild or moderate adhesions.

EXAMPLE 1

In the first series of experiments, nine rabbits were used. Four were vehicle controls in which the pumps contained isotonic buffer alone, and the other five were used to evaluate the efficacy of t-PA to combat post-surgical adhesion as described above. The mini pump in each t-PA test rabbit contained two ml of isotonic buffer containing 5 mg per ml of essentially pure t-PA. The results of the experiments are shown below in Table I:

TABLE I

| Rabbit No. | t-PA or Control | Adhesion Evaluation |
|---|---|---|
| 1 | Control | 5 |
| 2 | " | 5 |
| 3 | " | 4 |
| 4 | " | 5 |
| 5 | t-PA | 1* |
| 6 | " | 1* |
| 7 | " | 1 |
| 8 | " | 1* |
| 9 | " | 1 |

*Three of the rabbits exhibited bleeding at the site of the trauma; two bled lightly and the other moderately to severely.

EXAMPLE 2

In order to try to better define the threshold dosage rate in this experimental model, similar experiments were carried out with the mini pump, using different concentrations of t-PA per pump. Table II, below, sets forth the dosage rates and responses in this series of experiments:

TABLE II

| Rabbit No. | mg t-PA Per ml of Buffer | Adhesion Evaluation |
|---|---|---|
| 1 | 3 | 1 |
| 2 | 3 | 1 |
| 3 | 1.5 | 1 |
| 4 | 1.5 | 1 |
| 5 | 1.5 | 1 |
| 6 | 0.5 | 4 |
| 7 | 0.5 | 4 |
| 8 | 0.15 | 1 |
| 9 | 0.15 | 1 |
| 10 | 0.15 | 3 |
| 11 | 0.05 | 1 |
| 12 | 0.05 | 3 |
| 13 | 0.05 | 4 |
| 14 | 0.015 | 5 |
| 15 | 0.015 | 5 |
| 16 | 0.015 | 4 |

These results indicate that the threshold dosage (for this Genentech t-PA) at which significant beneficial anti-adhesion properties are obtained is between 0.015 and 0.05 mg t-PA/ml of buffer. (The results observed with rabbit Nos. 6 and 7 appear to be anomalous.) No bleeding was encountered with any of these rabbits.

Since no bleeding was encountered with any of the rabbits in the dosage rate studies, it appears that in this model and mode of administration, a safe upper limit of dosage that would not result in significant bleeding would be found in the dosage rate administered to Rabbit Nos. 1 and 2 (in which the concentration of t-PA was 3 mg/ml).

EXAMPLE 3

In order to determine the time period over which the anti-adhesion agent is preferably administered in order to have a significant anti-adhesion effect in the particular animal model and mode of administration used, the following series of experiments were carried out:

The pumps contained 10 mg of t-PA (5 mg/ml), and the catheter delivering the treatment solution to the site of the surgical trauma was disconnected 2, 3, and 5 days post-operatively. The rabbits were sacrificed 7 days post-operatively, and evaluated as above. The results are displayed in Table III, below.

TABLE III

| Rabbit No. | Post-Op Day Catheter Disconnected | Evaluation |
|---|---|---|
| 1 | 2 | 1 |
| 2 | 2 | 1 |
| 3 | 2 | 1 |
| 4 | 3 | 1 |
| 5 | 3 | 1 |
| 6 | 3 | 1 |
| 7 | 5 | 1 |
| 8 | 5 | 4 |
| 9 | 5 | 1 |

EXAMPLE 4

In this experiment, t-PA obtained from Damon Biotech, Needham Heights, Mass. This t-PA was predominantly single stranded t-PA. The experiment was similar to that described above in Example 2, except that a vehicle control site was used in each rabbit, as explained above in the Standardized Surgical Injury section. The results were as follows:

TABLE IV

| Rabbit No | mg t-PA per ml buffer | Evaluation t-PA Site | Vehicle Control Site |
|---|---|---|---|
| 1 | 0.5 | 1 | 5 |
| 2 | " | 1 | 5 |
| 3 | " | 1 | 1 |
| 4 | " | 1 | 5 |
| 5 | " | 3 | 4 |
| 6 | 0.15 | 1 | 1 |
| 7 | " | 1 | 1 |
| (Bleeding) | | | |
| 8 | " | 1 | 1 |
| 9 | " | 3 | 1 |
| 10 | " | 1 | 1 |
| 11 | 0.05 | 1 | 3 |
| 12 | " | 1 | 3 |
| 13 | " | 1 | 1 |
| 14 | " | 1 | 4 |
| 15 | " | 1 | 3 |
| 16 | 0.015 | 1 | 1 |
| 17 | " | 3 | 4 |
| 18 | " | 1 | 1 |
| 19 | " | 1 | 5 |
| 20 | " | 1 | 5 |

The Damon Biotech t-PA appears to be more active, on a weight basis, than the Genentech t-PA.

Urokinase and streptokinase were both evaluated for anti-adhesion activity in the rabbit model described above, and both were found to have no anti-adhesion activity.

It is relevant to note that when the vehicle control site is in the same rabbit as the test site, migration of fluid in the peritoneal cavity can carry some of the medicament from the treatment site to the vehicle control site. Therefore, it is possible that some vehicle control sites could have received small amounts of t-PA owing to migration or circulation of fluid within the peritoneal cavity. However, if any of the untreated control sites did receive some of the active medicament by such fluid migration, it would have been significantly less than that received at the treatment site in the same rabbit. Therefore, differences in results between the treatment sites and the control sites in the same rabbit can confidently be interpreted as being caused by the adhesion inhibition effect of the t-PA.

An effective dose of a topically applied drug is normally expressed in terms of concentration of the drug in the carrier, coupled with the number of times per day the drug is applied. In the present invention, the effective dose will be dependent upon factors such as nature of specific t-PA used, nature of vehicle, nature of tissue to be treated, type of trauma, and mode of delivery (i.e., continuous delivery by catheter or a one-time application in a vehicle such as a gel, ointment, salve, or controlled release vehicle). Therefore, no hard and fast rule can be formulated that will apply in all cases, and experiments analogous to those reported in Examples 2 and 4 will have to be performed in order to precisely define the threshold dosage for specific vehicle systems, for specific modes of delivery, etc. It is well within the ability of the person skilled in the art to carry out the necessary experiments to determine threshold dosages and periods of time over which the t-PA should be administered for best results, after having read this disclosure.

The t-PA active ingredient is administered to the site of surgical trauma topically. Such topical administration can be by spraying, lavage, dripping on the site, by catheter administration, or the like. The exact method of administration chosen is not critical, as long as an effective dose is administered over the appropriate period of time, which can be determined by a series of experiments analogous to that described above in Example 3.

Referring to the question of the effective dose of t-PA in accordance with this invention, while no hard and fast numbers can be presented that will be applicable to all cases, the examples presented above can be referred to as a guide to determine the order of magnitude of t-PA to employ. Thus, a concentration of t-PA in the vehicle of at least about 0.015 milligrams of t-PA per milliliter of total vehicle or carrier can be expected to exhibit anti-adhesion activity in most cases.

What is claimed is:

1. A process for inhibiting post-surgical adhesion formation in mammals which comprises the topical locally effective administration to the injured tissue surface site of surgical trauma of an effective amount of a sterile composition including as an active ingredient tissue plasminogen activator, for a period of time sufficient to inhibit the formation of post-surgical adhesions.

2. The process of claim 1 wherein such administration is made to the injured tissue site prior to closing the surgical field.

3. The process of claim 1 wherein the active ingredient is contained in a pharmaceutically acceptable organic carrier.

4. The process of claim 3 wherein said carrier is a phospholipid.

5. The process of claim 3 wherein said carrier is a phospholipid vesicle.

6. The process of claim 3 wherein said carrier is an absorbable polymer.

7. The process of claim 1 wherein said period is from about one hour to seven days.

8. The process of claim 1 wherein the active ingredient is contained in an aqueous solution of a surface active agent.

9. The process of claim 1 wherein the active ingredient is contained in an aqueous isotonic buffer solution.

10. The process of claim 1 wherein the tissue plasminogen activator is present in said composition at a concentration of at least about 0.015 milligram of tissue plasminogen activator per milliliter of said composition.

11. The process of claim 1 wherein the said composition comprises an aqueous solution or suspension of a pharmaceutically acceptable organic carrier.

12. The process of claim 11 wherein the organic carrier is a polymeric material.

13. The process of claim 11 wherein the organic carrier is a phospholipid.

14. The process of claim 11 wherein the organic carrier is a proteoglycan or water-soluble salt or ester thereof.

15. The process of claim 11 wherein the organic carrier is hyaluronic acid or water-soluble salt or ester thereof.

* * * * *